US012023313B2

(12) United States Patent
Peiris et al.

(10) Patent No.: US 12,023,313 B2
(45) Date of Patent: *Jul. 2, 2024

(54) METHOD OF TREATMENT OF OBESITY (71) Applicant: Queen Mary University of London, London (GB)

(72) Inventors: Madusha Peiris, London (GB); Ashley Blackshaw, London (GB)

(73) Assignee: Queen Mary University of London, London (GB)

( * ) Notice: Subject to any disclaimer, the term of this patent is extended or adjusted under 35 U.S.C. 154(b) by 127 days.

This patent is subject to a terminal disclaimer.

(21) Appl. No.: 17/156,894

(22) Filed: Jan. 25, 2021

(65) Prior Publication Data
US 2021/0251932 A1 Aug. 19, 2021

Related U.S. Application Data (63) Continuation of application No. 16/088,312, filed as application No. PCT/GB2017/050709 on Mar. 15, 2017, now Pat. No. 10,925,849.

(30) Foreign Application Priority Data

Mar. 15, 2016 (GB) ..................................... 1604377
Jul. 19, 2016 (GB) ..................................... 1612485

(51) Int. Cl.
*A61K 31/20* (2006.01)
*A61K 31/01* (2006.01)
*A61K 31/192* (2006.01)
*A61K 36/55* (2006.01)
*A61K 45/00* (2006.01)
*A61P 3/00* (2006.01)

(52) U.S. Cl.
CPC .............. *A61K 31/20* (2013.01); *A61K 31/01* (2013.01); *A61K 31/192* (2013.01); *A61K 36/55* (2013.01); *A61K 45/00* (2013.01); *A61P 3/00* (2018.01); *A61K 45/05* (2013.01)

(58) Field of Classification Search
CPC ........ A61K 31/202; A61K 31/192; A61P 3/04
See application file for complete search history.

(56) References Cited

U.S. PATENT DOCUMENTS

| 9,006,288 | B2 | 4/2015 | Szewczyk |
| 2006/0167094 | A1 | 7/2006 | Fleming et al. |
| 2007/0293481 | A1 | 12/2007 | Seed et al. |
| 2009/0111876 | A1 | 4/2009 | Hsieh |

FOREIGN PATENT DOCUMENTS

| EP | 1891963 | 2/2008 |
| EP | 2116238 | 11/2009 |
| FR | 2927771 | 8/2009 |
| KR | 2015056348 A | * 5/2015 |
| WO | 200224180 | 3/2002 |
| WO | 2007134613 | 11/2007 |
| WO | 2009109973 | 9/2009 |
| WO | 2010027433 | 3/2010 |
| WO | 2010102041 | 9/2010 |
| WO | 2011072132 | 6/2011 |
| WO | 2014059232 | 4/2014 |
| WO | 2014069963 | 5/2014 |
| WO | 2015181640 | 12/2015 |

OTHER PUBLICATIONS

Abdel-Magid, "Therapeutic Potential of GPR120 Agonists for the Treatment of Type 2 Diabetes", ACS Med Chem Lett, 2015, 6, pp. 1097-1098.
Bueter et al., "Gastrointestinal hormones, energy balance and bariatric surgery", International Journal of Obesity, 2011, 35, pp. 535-539.
Chambers et al., "Effects of targeted delivery of propionate to the human colon on appetite regulation, body weight maintenance and adiposity in overweight adults", Gut, 2015, 64, pp. 1744-1754.
Feltrin et al., "Effects of intraduodenal fatty acids on appetite, antropyloroduodenal motility, and plasma CCK and GLP-1 in humans vary with their chain length", Am J Physiol Regul Integr Comp Physiol, 2004, 287, pp. R524-R533.
Feltrin et al., "Comparative effects of intraduodenal infusions of lauric and oleic acids on antropyloroduodenal motility, plasma cholecystokinin and peptide YY, appetite, and energy intake in healthy men", Am J Clin Nutr, 2008, 87, pp. 1181-1187.
Hirasawa et al., "Free fatty acids regulate gut incretin glucagon-like peptide-1 secretion through GPR120", Nature Medicine, 2005, 11(1), pp. 90-94.
Ichimura et al., "Dysfunction of lipid sensor GPR120 leads to obesity in both mouse and human", Nature, 2012, 483, pp. 350-357.
Liu et al., "Design and Synthesis of 2-Alkylpyrimidine-4,6-diol and 6-Alkylpyridine-2,4-diols as Potent GPR84 Agonists", ACS Med Chem Lett, 2016, 7, pp. 579-583.
Ma et al., "A randomised trial of enteric-coated nutrient pellets to stimulate gastrointestinal peptide release and lower glycaemia in type 2 diabetes", Diabetologia, 2013, 56, pp. 1236-1242.
Oh et al., "The role of G-protein-coupled receptors in mediating the effect of fatty acids on inflammation and insulin sensitivity", Current Opinion in Clinical Nutrition and Metabolic Care, 2011, 14, pp. 322-327.
Oh et al., "A Gpr120-selective agonist improves insulin resistance and chronic inflammation in obese mice", Nature Medicine, 2014, 20(8), pp. 942-949.
Segura-Campos et al., "Chemical and Functional Properties of Chia Seed (*Salvia hispanica* L.) Gum", International Journal of Food Science, 2014, pp. 1-5.

(Continued)

*Primary Examiner* — Shobha Kantamneni
(74) *Attorney, Agent, or Firm* — Armstrong Teasdale LLP (57) ABSTRACT

The present invention provides compositions and pharmaceutical compositions of GPR84 agonists and GPR120 agonists for use in the treatment of obesity and overweight. The invention provides methods of treatment accordingly as well as a kit for use in the treatment of obesity and overweight.

8 Claims, 8 Drawing Sheets

(56) References Cited

OTHER PUBLICATIONS

Symonds et al., Mechanisms of activation of mouse and human enteroendocrine cells by nutrients, Gut, 2015, 64, pp. 618-626.
Tan et al., "Pharmacokinetics, adverse effects and tolerability of a novel analogue of human pancreatic polypeptide, pp. 1420", British Journal of Clinical Pharmacology, 2011, 73(2), pp. 232-239.
Ulven et al., "Dietary Fatty Acids and Their Potential for Controlling Metabolic Diseases Through Activation of FFA4/GPR120", Annu Rev Nutr, 2015, 35, pp. 239-263.
Varum et al., "A novel coating concept for ileo-colonic drug targeting: Proof of concept in humans using scintigraphy", European Journal of Pharmaceutics, 2013, 84, pp. 573-577.
Vieira et al., "Microwave synthesis and in vitro stability of diclofenac-[beta]-cyclodextrin conjugate for colon delivery", Carbohydrate Polymers, 2013, 93, pp. 512-517.
Wang et al., "Medium-chain Fatty Acids as Ligands for Orphan G Protein-coupled Receptor GPR84*", The Journal of Biological Chemistry, 2006, 281(45), pp. 34457-34464.
Shimpukade et al., "Discovery of a Potent and Selective GPR120 Agonist", J Med Chem, 2012, 55, pp. 4511-4515.
Chaudhari et al., "Preventive Effect of Embelin from Embelia ribes on Lipid Metabolism and Oxidative Stress in High-Fat Diet-Induced Obesity in Rats", Planta Medica, 2012, 78(7), pp. 651-657.
Oh et al., "GPR120 Is an Omega-3 Fatty Acid Receptor Mediating Potent Anti-inflammatory and Insulin-Sensitizing Effects", 2010, 142(5), pp. 687-698.
Wellendorph et al., "Molecular Pharmacology of Promiscuous Seven Transmembrane Receptors Sensing Organic Nutrients", Molecular Pharmacology, 2009, 76(3), pp. 453-465.
Licznerska et al., "Indole-3-Carbinol and Its Role in Chronic Diseases", Advances in Experimental Medicine and Biology, 2016, 928, pp. 131-154.
Hudson et al., "The Pharmacology of TuG-891, a Potent and Selective Agonist of the Free Fatty Acid Receptor 4 (FA4/GPR120), Demonstrates Both Potential Opportunity and Possible Challenges to Therapeutic Agonism", Mol. Pharmacol, 2013, 84, pp. 710-725.

* cited by examiner

METHOD OF TREATMENT OF OBESITY

The present invention relates to a method of treatment of obesity. Compositions useful in the treatment of obesity and related conditions are also described.

Obesity and overweight are some of the major heath challenges faced by modern medicine and society. The common health consequences of overweight and obesity are defined by the World Health Organisation in 2016 as cardiovascular diseases (mainly heart disease and stroke), which were the leading cause of death in 2012; diabetes; musculoskeletal disorders (especially osteoarthritis); and some cancers (endometrial, breast, and colon).

Bypass surgery is an effective treatment for obesity and type II diabetes. It works by shunting ingested food directly to the lower part of the gut, whereupon unabsorbed nutrients stimulate the release of gut hormones from cells lining the gut. These hormones reduce the feeling of hunger in the brain, and they simultaneously stimulate the pancreas to produce insulin (Bueter & le Roux Int J Obes (Lond) 35 Suppl 3:S35-9 (2011)). Exactly which nutrients cause this effect, and exactly which hormones they release, and how, are not fully understood.

Current protein-based approaches to weight loss use large oral loads which contain significant caloric value. They stimulate only one part of the system and are mostly or entirely absorbed before reaching the lower gut. Therefore reduction in food intake is minimal and the formulation has to be prepared by the subject making it inconvenient. It is also unpalatable and compliance is low.

Other weight-loss therapies include the use of lipase inhibitors such as Orlistat® and protein shakes such as Myprotein®. Also synthetic pancreatic polypeptide, which is being developed as a subcutaneous treatment ((Tan et al. Br J Clin Pharmacol 2012; 73:232-9)).

Targeted release formulations of drugs for delivery into the lumen of the intestine are available. Recent developments now allow them to be released specifically within the large intestine (Varum et al Eur J Pharm Biopharm. 84(3): 573-7 (2013)). So far these formulations have been designed to deliver anti-inflammatory drugs for treatment of inflammatory bowel disease (Vieira et al Carbohydr Polym. 93:512-7 (2013)). Interest is however growing in the use of this technology for delivery of nutrients known to activate enteroendocrine cells, in order to treat obesity (Chambers et al Gut 64(11):1744-54 (2015) and doi: 10.1136/gutjnl-2014-307913. Epub 2014 Dec. 10) 3 and type II diabetes (Ma et al Diabetologia 56:1236-42 (2013)). Attempts to treat obesity in this manner have so far been unsuccessful.

Lauric acid (a component of coconut oil), when infused into the small intestine through a nasogastric tube, reduces food intake more potently than other fatty acids (Feltrin et al Am J Physiol Regul Integr Comp Physiol 287:R524-33 (2004); Feltrin et al Am J Clin Nutr 87:1181-7 (2008)).

It does this by increasing plasma levels of gut hormones like peptide YY (PYY) and glucagon-like peptide-1 (GLP-1). There is evidence that the receptor for lauric acid, known as GPR84 (Oh & Lagakos Curr Opin Clin Nutr Metab Care 14:322-7 (2011); Wang et al J Biol Chem 281:34457-64 (2006)), is localised on serotonin and PYY/GLP-1 containing enteroendocrine cells in the human intestine (Symonds et al. Gut 64:618-26 (2015)).

It has also been shown that lauric acid activates a downstream signalling pathway in these cells involving phosphorylated extracellular signal related kinase (pERK), whereas other nutrients may activate the same cells, but not via pERK. Instead they activate pCalmodulin kinase II (pCAM-KII), which is a parallel pathway to pERK. One such nutrient is α-linolenic acid, a component of flaxseed oil, acting via a specific receptor—GPR120. GPR120 knockout mice are obese, and there is great interest in this receptor for treatment of obesity (Ichimura et al Nature 483:350-4 (2012); Ulven & Christiansen Annu. Rev. Nutr., 35, 239-263 (2015)) or diabetes (Hirasawa et al Nature Medicine, 11(1), 90-94 (2005)).

There is therefore a need for a treatment for obesity and overweight which is safe and effective.

According to a first aspect of the invention, there is provided a composition comprising a GPR84 agonist and a GPR120 agonist for use in the treatment of obesity and overweight. References to a GPR84 agonist and a GPR120 agonist include variants and derivatives thereof. Where the GPR84 agonist or the GPR120 agonist is a fatty acid molecule suitable variants and derivatives include esters thereof. Esters of fatty acids can be formed with any organic compound containing a hydroxyl functional group such as an alcohol. Esters formed with glycerol include mono-, di-, and tri-glycerides. References herein to esters therefore include the corresponding mono-, di-, and/or tri-glycerides of the fatty acid or molecule concerned. The agonists may be full or partial agonists.

GPR84 agonists include medium-chain free fatty acid (FFA) with carbon chain lengths of C9 to C14, for example lauric acid (C12:0), pelargonic acid (C9:0), capric acid (C10:0), undecanoic acid (C11:0); tridecanoic acid (C13:0) and myristic acid (C14:0), or an ester thereof, and other compounds such as 3,3'-diindolylmethane (also known as 3,3'-methanediylbis(1H-indole)).

In one embodiment, the GPR84 agonist is selected from the group consisting of lauric acid (C12:0), undecanoic acid (C11:0) and capric acid (C10:0), or an ester thereof. Suitably, the GPR84 agonist is lauric acid.

Other GPR84 agonists include 2-pentylthiopyrimidine-4, 6-diol, 6-nonylpyridine-2,4-diol, embelin (undecyl-1,4-benzoquinone), or an ester thereof. A series of 2-alkylpyrimidine-4,6-diol derivatives are described in Liu et al ACS Med. Chem. Lett. 30 Mar. 2016 (DOI: 10.1021/acsmedchemlett.6b00025).

GPR120 agonists include omega-3 fatty acids, or an ester thereof and other analogue compounds such as [3-(4-((4-fluoro-4'-methyl-[1,1'-biphenyl]-2-yl)methoxy) phenyl)propanoic acid (TUG891), or an ester thereof. Omega-3 fatty acids are polyunsaturated fatty acids (PUFAs), for example α-linolenic acid (ALA), eicosapentaenoic acid (EPA) and docosahexaenoic acid (DHA), or an ester thereof.

α-linolenic acid (ALA) contains 3 unsaturated carbon-carbon double bonds (n-3) and is also known as (9Z,12Z, 15Z)-9,12,15-Octadecatienoic acid or cis,cis,cis-9,12,15-Octadecatrienoic acid. It is also sometimes referred to as 18:3.

Eicosapentaenoic acid (EPA) (or icosapentaenoic acid) is sometimes referred to as 20:5 (n-3). The formal name of the molecule is (5Z,8Z,11Z,14Z,17Z)-5,8,11,14,17-icosapentaenoic acid.

Docosahexaenoic acid (DHA) is also known as (4Z,7Z, 10Z,13Z,16Z,19Z)-docosa-4,7,10,13,16,19-hexaenoic acid and comprises 6 unsaturated carbon-carbon double bonds 22:6 (n-3).

Other GPR120 agonists include 4-Methoxy-N-(2,4,6-trimethylphenyl)benzenesulfonamide, 4-(4-{2-[phenyl (pyridin-2-yl)amino]ethoxy}phenyl)butanoic acid, 3-(4-((4-Fluoro-4'-methyl-(1,1'-biphenyl)-2-yl)methoxy)-phenyl) propanoic acid (Oh Nature Medicine, 20(8) 942-949 (2014)) and grifolic acid, or an ester thereof. Other GP120 agonists are disclosed in WO 2015/134039 which described a class of isothiazole derivatives (see also Abdel-Magid *ACS Med. Chem. Lett.*, 6, 1097-1098 (2015)) or an ester thereof.

The GPR120 agonist can be derived from a natural (non-synthetic) source, for example plant seeds, suitably in the form of an oil prepared from the seeds, i.e. a plant seed oil. Alternatively, the GPR120 agonist may be synthesised using chemical or biological means.

Suitably, the natural source of the oil contains at least 50% ALA, or at least 60%, 65% or 70% ALA. Examples of suitable plant seed oils are linseed oil and chia seed oil. One example of linseed oil contains 68.2% ALA (Segura-Campos et al., Int J Food Sci, 2014).

Linseed oil, also known as flaxseed oil, is obtained from the dried ripened seeds of the flax plant. Linseed oil comprises primarily of the unsaturated fatty acids α-linolenic acid, linoleic acid and oleic acid. For example, α-linolenic acid can be present in the amount 50%-75%, linoleic acid can be present in the amount 10%-25% and oleic acid can be present in the amount 10%-35%.

For example linseed oil may comprise 53.21% α-linolenic acid, 17.25% linoleic acid and 18.51% oleic acid.

GPR120 may also be referred to as free fatty acid receptor 4 (FFA4) or (FFA4/GPR120).

In another embodiment of the invention, the composition may comprise a plurality of GPR84 agonists and a GPR120 agonist. Suitably, the composition may comprise a pair of GPR84 agonists and a GPR120 agonist. For example, the composition may comprise 3,3'-diindolylmethane/lauric acid (DIM/LA) and α-linolenic acid (ALA).

The compositions of the invention upregulate both extracellular signal-regulated kinase in its phosphorylated form (pERK) and calmodulin kinase in its phosphorylated form (pCaMKII) which therefore increases the number of activated cells compared to a single treatment with a single agonist alone. A combination formula is therefore able to maximally activate both L-cells and EC cells in human intestinal tissue.

L-cells are a specialised form of enteroendocrine cells which secrete glucagon-like peptide-1 (GLP-1), peptide YY (PYY), oxyntomodulin and glucagon-like peptide-2 (GLP-2). EC cells are enterochromaffin cells or "Kulchitsky cells" that release serotonin.

Compositions of the invention comprising a GPR84 agonist and a GPR120 agonist may be formulated as convenient for administration to a patient in need thereof.

The composition of the invention may be provided in the form of a pharmaceutical composition. The composition may be prepared as a liquid, a solid, or a powder as convenient.

The pharmaceutical composition may be administered in any effective, convenient manner effective for treating obesity including, for instance, administration by oral, nasogastric tube, rectal, intraperitoneal, or intravenous, mutes among others. It is envisaged that the compositions of the invention will find greatest application as orally administrable formulations or as a suppository. The composition may also be administered to an individual as a liquid composition, for example as a sterile dispersion for administration via a nasogastric tube or a stoma.

The composition may be formulated with such additional salts, preservatives and stabilisers and/or excipients or adjuvants as required. For example, amino acids may be present in the formulation. The amino acid may be one or more selected from the group consisting of: Glycine, Alanine, Valine, Leucine, Isoleucine, Serine, Cysteine, Selenocysteine, Threonine, Methionine, Proline, Phenylalanine, Tyrosine, Tryptophan, Histidine, Lysine, Arginine, Aspartate, Glutamate, Asparagine, and Glutamine. An example of a preservative is Vitamin E, including isomers and derivatives thereof, e.g. α-tocopherol, γ-tocopherol, d-alpha-tocopherol succinate.

The formulation may be provided in a capsule, for example in a delayed release capsule and where suitably said capsule will disintegrate only upon reaching the large intestine or terminal part of the small intestine. Suitably, the delayed release capsule is a colonic release capsule in which the contents are preferentially released in the colon.

Such capsules can be administered prior to a meal, for example approximately 30 minutes before a meal. Suitable delayed release capsules can be prepared using anionic polymers of suitable monomers that degrade preferentially in a pH of 7.0 or above. Examples of such suitable monomers are methacrylic acid and methyl methacrylate (e.g. sold under the trade name Eudragit® by Evonik Industries). The capsule may therefore be composed of a polymer of methacrylic acid and methyl methacrylate.

Such capsules can be designed to release sufficient fatty acid to achieve local intraluminal concentrations of >25 mmol/L, which has been shown to be optimal for stimulation of enteroendocrine cells and consequent release of gut satiety hormones.

Alternatively, the composition may be formulated as an emulsion, suitably in the presence of an emulsifying agent, or with starch.

In one embodiment, there is provided a liquid formulation of lauric acid and α-linolenic acid.

Powder forms of the composition may be prepared in tablet, mini-tablet, pellet or granule form (usually filled into capsule shells) form for oral administration. The tablets may be coated with a suitable enteric coating in order to pass through the stomach of the patient for release of the composition in the small intestine. Suitable enteric coatings include, but are not limited to methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, alginate, e.g. sodium alginate, zein (maize protein).

Administration of the GPR84 agonist and the GPR120 agonist may be separate, sequential or simultaneous. According to a second aspect of the invention, there is provided a composition comprising a GPR84 agonist and a GPR120 agonist as a combined preparation for simultaneous, separate or sequential use in the treatment of obesity and overweight.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, caprine, porcine, bovine and equine families.

According to the present invention, the treatment of obesity includes prophylactic (preventive) treatment for patients at risk of the condition as well as the therapeutic treatment for patients after obesity and overweight has developed.

For administration to mammals, and particularly humans, it is expected that the daily dosage of the GPR84 agonist will be in the range of from about 1000 mg to about 5000 mg, optionally from about 1500 mg to about 3000 mg per day, for example about 1000 mg per day or about 2000 mg per day and the GPR120 agonist will be in the range of from about 100 mg to 5000 mg, optionally from about 150 mg to about 2000 mg per day, for example about 1000 mg per day.

Where a pair of GPR84 agonists are present in the composition, the second GPR84 agonist may be present in an amount of from 50 mg to 300 mg.

Suitable dosage forms may therefore be prepared as dosages at 100 mg, 150 mg, 1000 mg, 1500 mg, 2000 mg, 3000 mg or 5000 mg.

In one embodiment, the invention provides for a delayed release Eudragit® formulation specific for distal small intestine and large intestine (for example Eudragit® S 100), containing a mixture of fatty acids and amino acids—e.g. 1000 mg lauric acid and 1000 mg α-linolenic acid or about 2000 mg lauric acid and 1000 mg α-linolenic acid.

The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

The frequency of dosage may be varied as required but it may be suitable to administer the composition prior to eating a food meal. The composition may administered up to 90 minutes prior to a food meal, up to 60 minutes prior to a food meal, or up to 30 minutes prior to a food meal. The composition may be administered before two standard food meals up to 4 hours apart.

In one dosage regime, 2 capsules as defined above (e.g. 1000 mg lauric acid and 1000 mg α-linolenic acid or 2000 mg lauric acid and 1000 mg α-linolenic acid) can be taken 30 minutes before a meal is eaten by the patient.

In the case of linseed oil as the source of the GPR120 agonist, dosages may be from 500 mg to 5000 mg per day.

According to a third aspect of the invention, there is provided a method of treatment of obesity and overweight, comprising the step of administering to a patient in need thereof a composition as defined above. The present invention therefore extends to such compositions for use in the treatment of obesity and overweight.

According to a fourth aspect of the invention, there is provided the use of a GPR84 agonist and a GPR120 agonist in the manufacture of a medicament for use in the treatment of obesity and overweight.

Obesity is defined by the World Health Organisation (WHO) as abnormal or excessive fat accumulation that may impair health, where a Body Mass Index (BMI) of greater or equal to 30 is defined as obesity.

Overweight is defined by the World Health Organisation (WHO) as abnormal or excessive fat accumulation that may impair health, where a Body Mass Index (BMI) greater than or equal to 25 is overweight.

Body mass index (BMI) is an index of weight-for-height that can be used to classify overweight and obesity in adults. It is defined as a person's weight in kilograms divided by the square of his height in meters ($kg/m^2$).

According to a fifth aspect of the invention, there is provided a kit comprising a GPR84 agonist and a GPR120 agonist and optionally an administration vehicle, and/or instructions for use.

Without wishing to be bound by theory, it is believed that the present invention overcomes the problems encountered with previous approaches because it activates two parallel satiety pathways simultaneously.

It seems that co-localisation of GPR84 and GPR120 on human enteroendocrine cells, and that co-activation of both causes a super additive activation of pERK and pCAMKII. This means it is possible to boost gut hormone responses to those seen after gastric bypass, which is not achievable with one stimulus alone (Ma et al. Diabetologia 56:1236-42 (2013)).

The present invention offers a combination of nutrients to achieve super-additive activation of enteroendocrine responses. The formulations can be prepared for delivery to distal gut only. The compositions of the invention provide for a reduced dose of the therapeutic agent. The invention can achieve these advantages by virtue of the compositions being administered as a capsule and containing a minimal caloric load but which maximises satiety by acting in the lower gut.

The invention may find significant use in individuals without bowel disease wishing to lose weight.

Exemplary formulations may comprise:

LA/ALA Formulation
Lauric acid—1500 mg to about 3000 mg
α-linolenic acid—150 mg to about 2000 mg
Vitamin E—1 to 5%
DIM/ALA Formulation
3,3'-diindolylmethane—100 mg to about 250 mg
α-linolenic acid—150 mg to about 2000 mg
Vitamin E—1 to 5%
DIM/ALA Formulation
3,3'-diindolylmethane—50 mg to about 300 mg
α-linolenic acid—150 mg to about 2000 mg
Vitamin E—1 to 5%
LA/DIM/ALA Formulation
Lauric acid—1500 mg to about 3000 mg
3,3'-diindolylmethane—50 mg to about 300 mg
α-linolenic acid—150 mg to about 2000 mg
Vitamin E—1 to 5%
Linseed Oil/ALA Formulation
Linseed oil—500 mg to about 5000 mg
α-linolenic acid—150 mg to about 2000 mg
Vitamin E—1 to 5%

Suitably the formulations are encapsulated in a capsule composed of a polymer of methacrylic acid and methyl methacrylate monomers.

Preferred features of the second and subsequent aspects of the invention are as for the first aspect mutatis mutandis.

The invention will now be further described by way of illustration with reference to the following Examples and drawings in which.

EXAMPLE 1: CO-EXPRESSION OF NUTRIENT RECEPTORS GPR120 AND GPR84 ON L-CELLS (CONTAINING GLP-1) AND ENTEROCHROMAFFIN CELLS (CONTAINING 5-HT)

Figure 1:
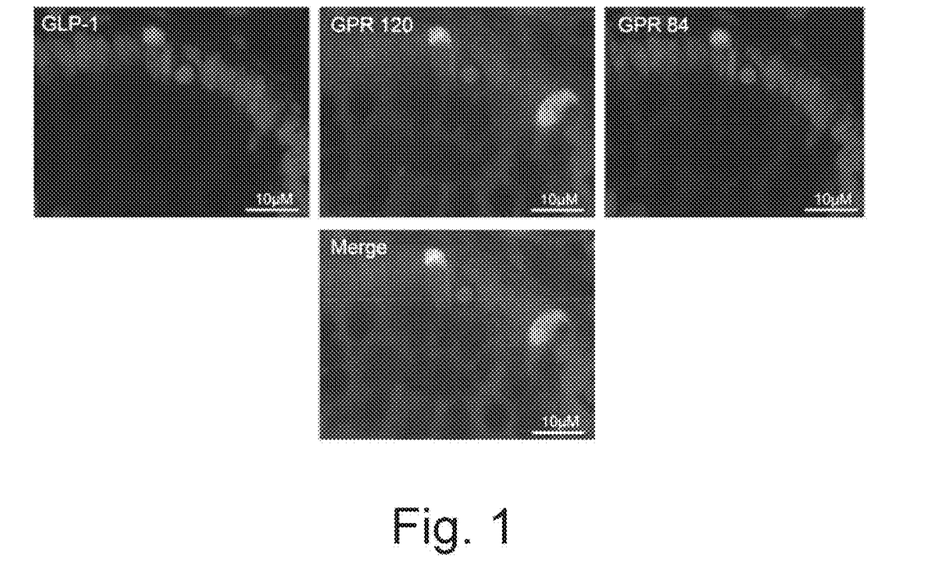
FIG. 1 shows L-cells co-express GPR120 and GPR84.
Figure 2:
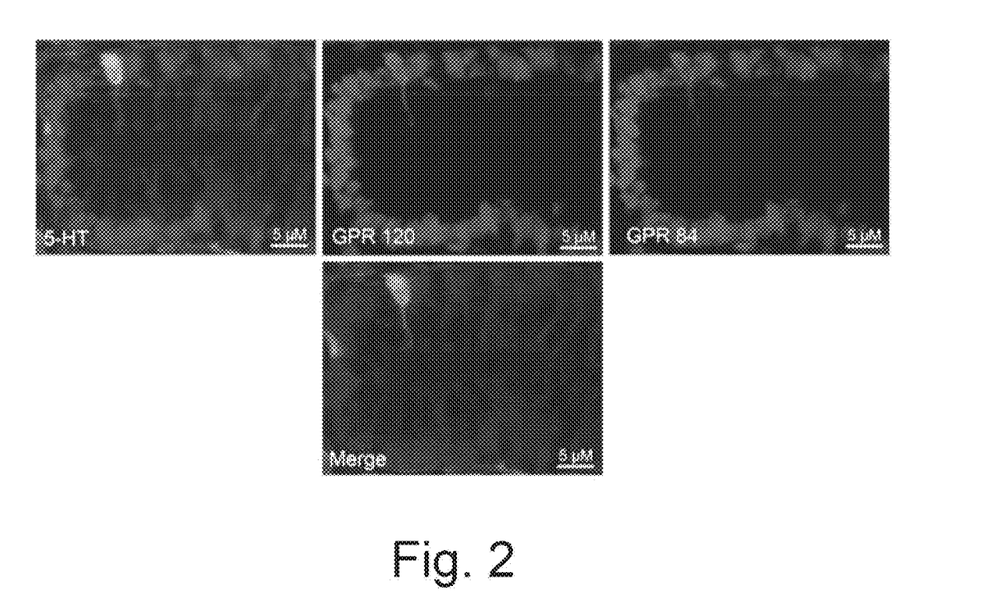
FIG. 2 shows Enterochromaffin cells co-express GPR120 and GPR84.
Figure 3:
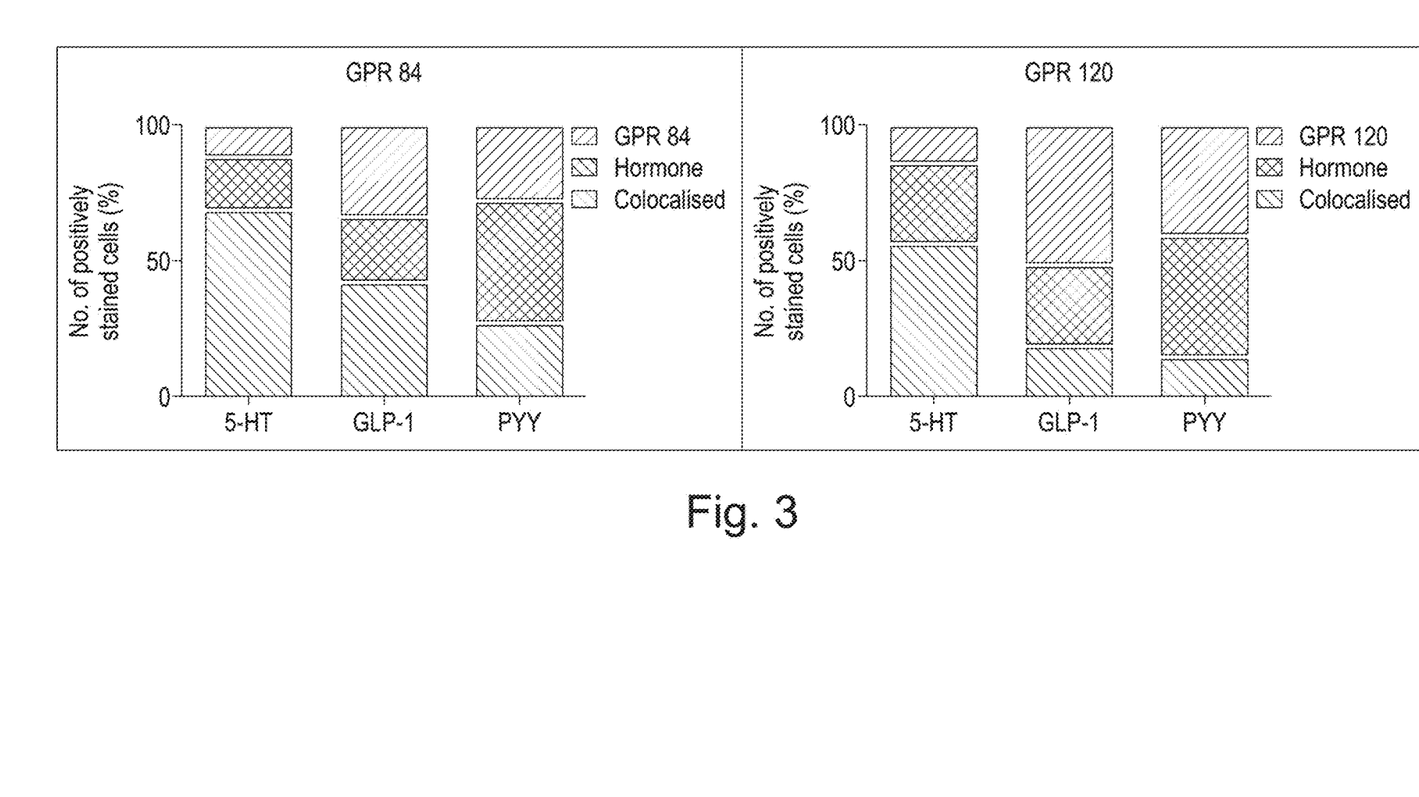
FIG. 3 shows GPR84 and GPR120 are predominantly expressed on 5-HT containing EC cells alongside L-cells albeit to a lesser extent.

The co-expression of nutrient receptors GPR120 and GPR84 on L-cells (containing GLP-1) and enterochromaffin cells (containing 5-HT) was examined using triple staining immunohistochemistry on human proximal colon. FIG. 1 demonstrates that both receptors are expressed on the basal side of L-cells (red). FIG. 2 shows enterochromaffin cells (green) express both receptors all around the cell, including the long process that extends into the lumen and has direct contact with luminally available nutrients. It was found that both GPR84 and GPR120 were highly expressed in 5-HT containing enterochromaffin cells (EC) in addition to being expressed on L-cells (with GLP-1 and PYY) (FIG. 3).

EXAMPLE 2: GPR120 AGONIST PREFERENTIALLY ACTIVATES A DIFFERENT INTRACELLULAR PATHWAY DRIVEN BY PHOSPHORYLATED CaMKII

Figure 4:
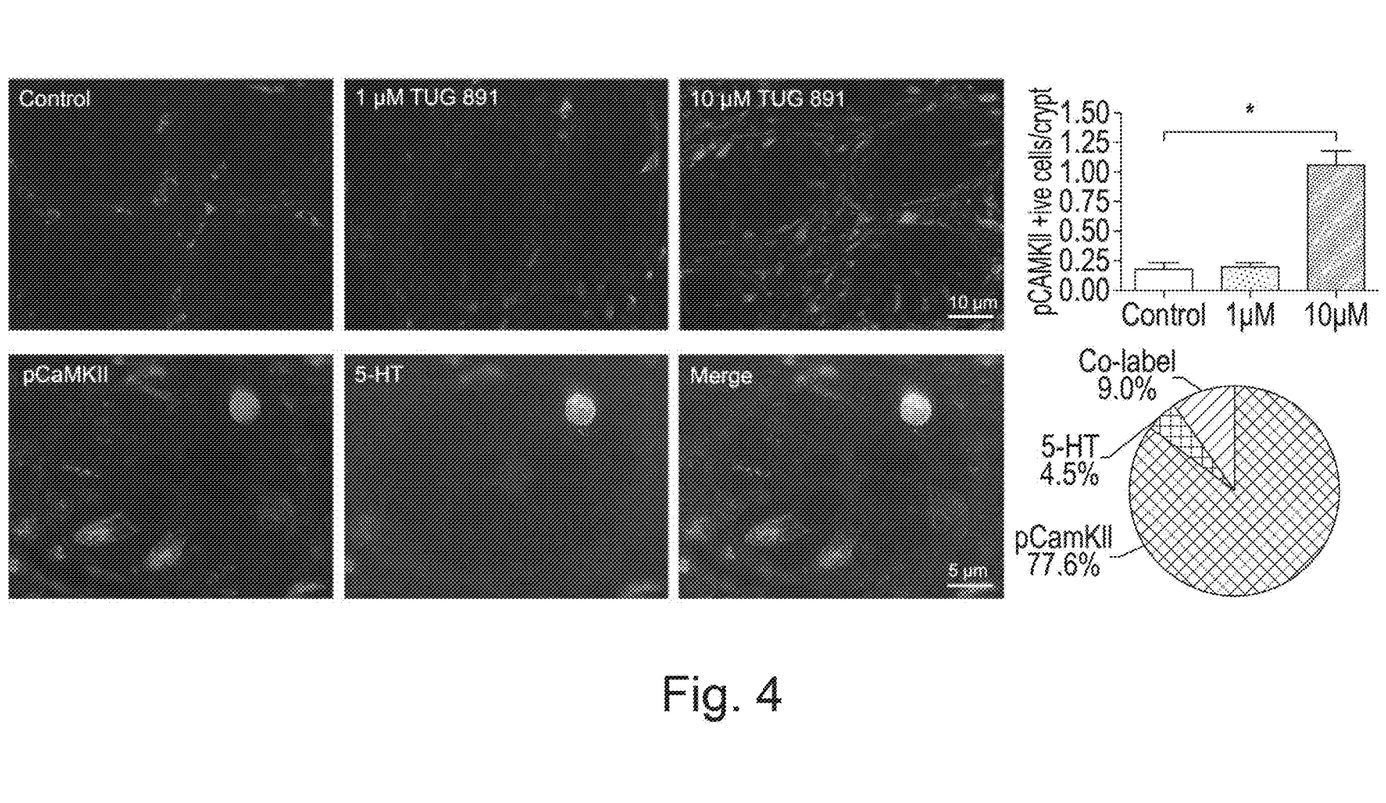
FIG. 4 shows Top panel—TUG891 significantly increases cellular activation as measured by expression of pCAMKII at 10 μM compared to control (N=3, p<0.05). Bottom panel—5-HT positive cells are activated following stimulation with TUG891 as shown by merge image.
Figure 5:
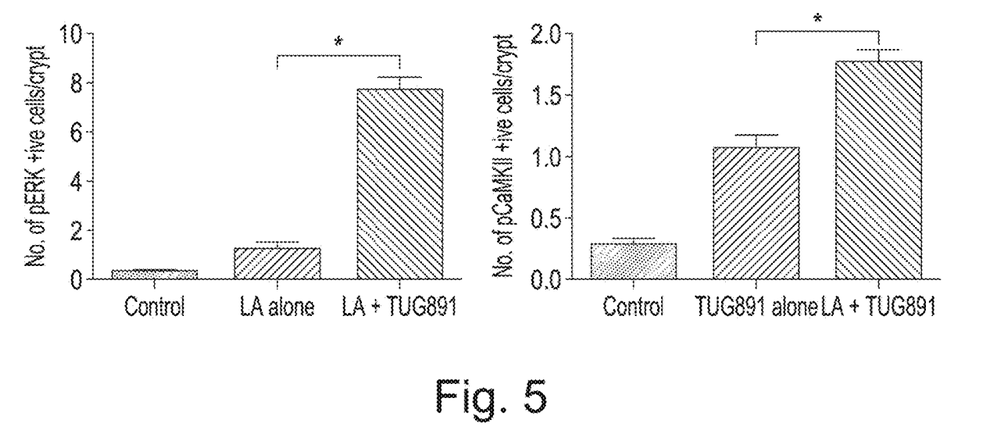
FIG. 5 shows stimulating human proximal colon with a combination of LA and TUG891 significantly increased the activation of both pERK and pCamKII suggesting increased overall activation of colonic epithelial cells. (N=3, n=15, p<0.05).

Previously it has been shown (Symonds, Peiris, et al, Gut 2014) that stimulation of human colonic mucosa with lauric acid (GPR84 agonist) activates an intracellular pathway as measured by phosphorylated ERK. The present results show TUG891 (GPR120 agonist) preferentially activates a different intracellular pathway driven by phosphorylated CaMKII, with some activated cells identified as EC cells (FIG. 4).

EXAMPLE 3: COMBINATION FORMULATION FOR ACTIVATION OF L-CELLS AND EC CELLS IN HUMAN PROXIMAL COLONIC SHEETS

Figure 6:
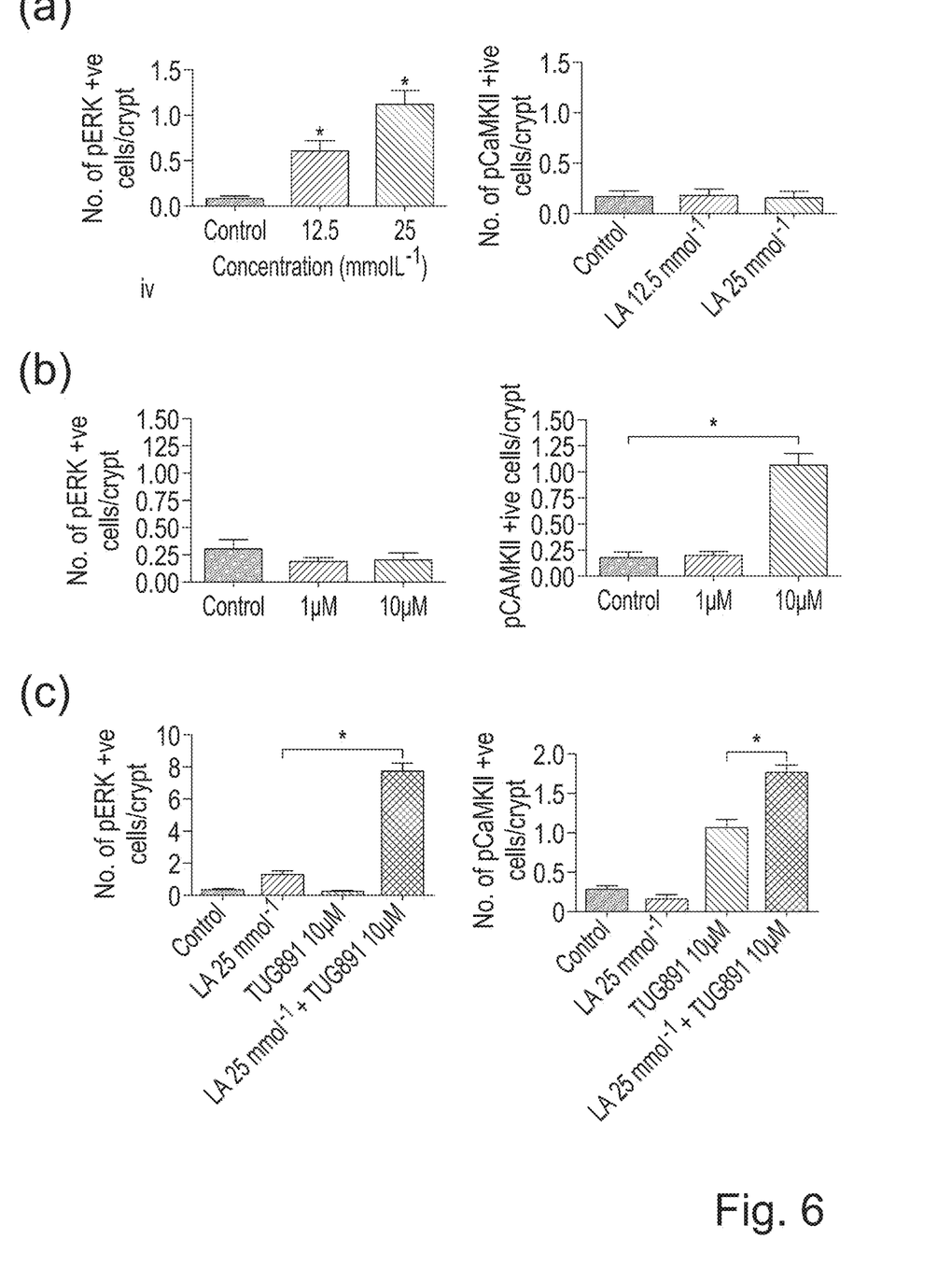
FIG. 6 shows synergistic effect of compositions of the invention (a) cell activation by Lauric Acid (LA) alone when administered at 12.5 $mmol^{-1}$ and 25 $mmol^{-1}$ compared to a control; (b) TUG891 alone when administered at 1 µM and 10 µM compared to a control; and (c) LA plus TUG891 in combination (25 mmol$^{-1}$ LA and 10 µM TUG891) compared to a control and LA at 25 mmol$^{-1}$ or TUG891 at 10 µM when administered alone.
Figure 7:
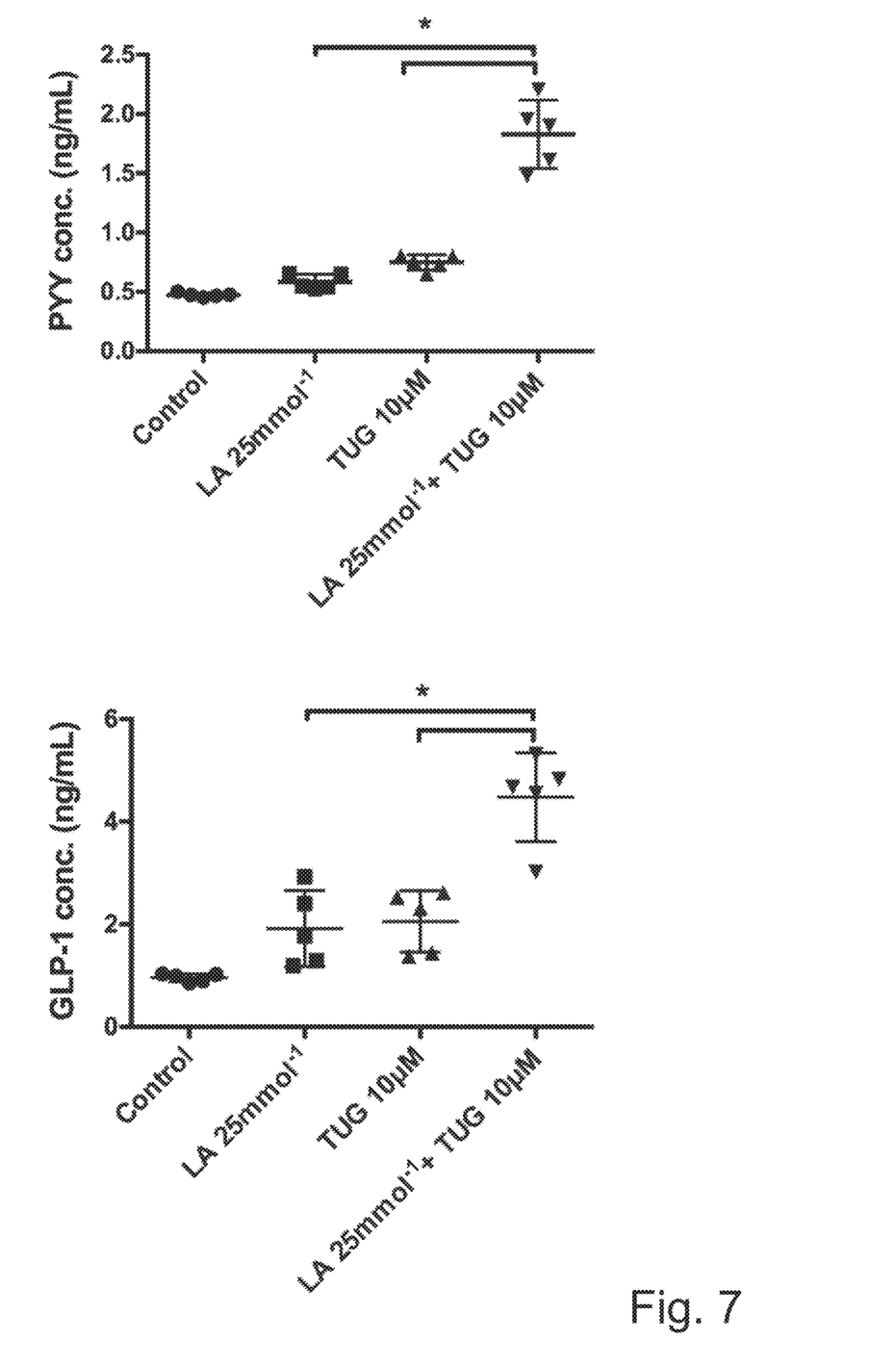
FIG. 7 shows hormone release profile from cells of PYY and GLP-1 for compositions of the invention using Lauric Acid (LA) and TUG891 (TUG).

The present results also show that both pERK and pCaMKII are up-regulated demonstrating that a combination of nutrients is able to increase the number of activated cells compared to a single nutrient treatment (FIG. 6). Importantly, increased numbers of activated L-cells are able to maximally release their contents, the hormones GLP-1 and PYY when stimulated by a combination formula i.e. lauric acid and TUG891, in human proximal colonic sheets (FIG. 7).

EXAMPLE 4: PATIENT TRIALS OF FORMULATIONS

The compositions of the invention are to be tested in patients in the following scheme.
1$^{st}$ Stage Acute
Objective: to test efficacy of modified release capsule of combination nutrients on metabolic parameters in obese type 2 diabetics
Design: Randomised Double-blind Placebo-controlled Crossover of 20 overweight volunteers. (1 g, 2 g and 5 g dosage, 60 min before 2 standard meals 4 hr apart, 2 weeks between trials)
Outcomes:
postprandial satiety questionnaire, plasma gut hormone, 5-HT, glucose and insulin profile
2$^{nd}$ Stage Chronic
Type: Phase IIb.
Objective: to test efficacy of modified release capsule of combination nutrients on weight loss and glycemic control
Design: Randomised Double-blind Placebo-controlled Parallel Pilot trial with 20 overweight volunteers. (Dosage will be based on data obtained from stage 1 trial, 60 min pre-prandial b.i.d.). No run-in or wash-out
Outcomes:
1°—Weight loss over 24 week administration
2°—Body fat mass, glycated haemoglobin (HbA1c), fasting blood glucose concentration (BGC).

EXAMPLE 5: GPR84 AGONIST 3,3'-DIINDOLYLMETHANE (DIM) POTENTLY ACTIVATES PERK IN COMBINATION WITH GPR120 AGONIST TUG891 AND GPR84 AGONIST LAURIC ACID

Figure 8:
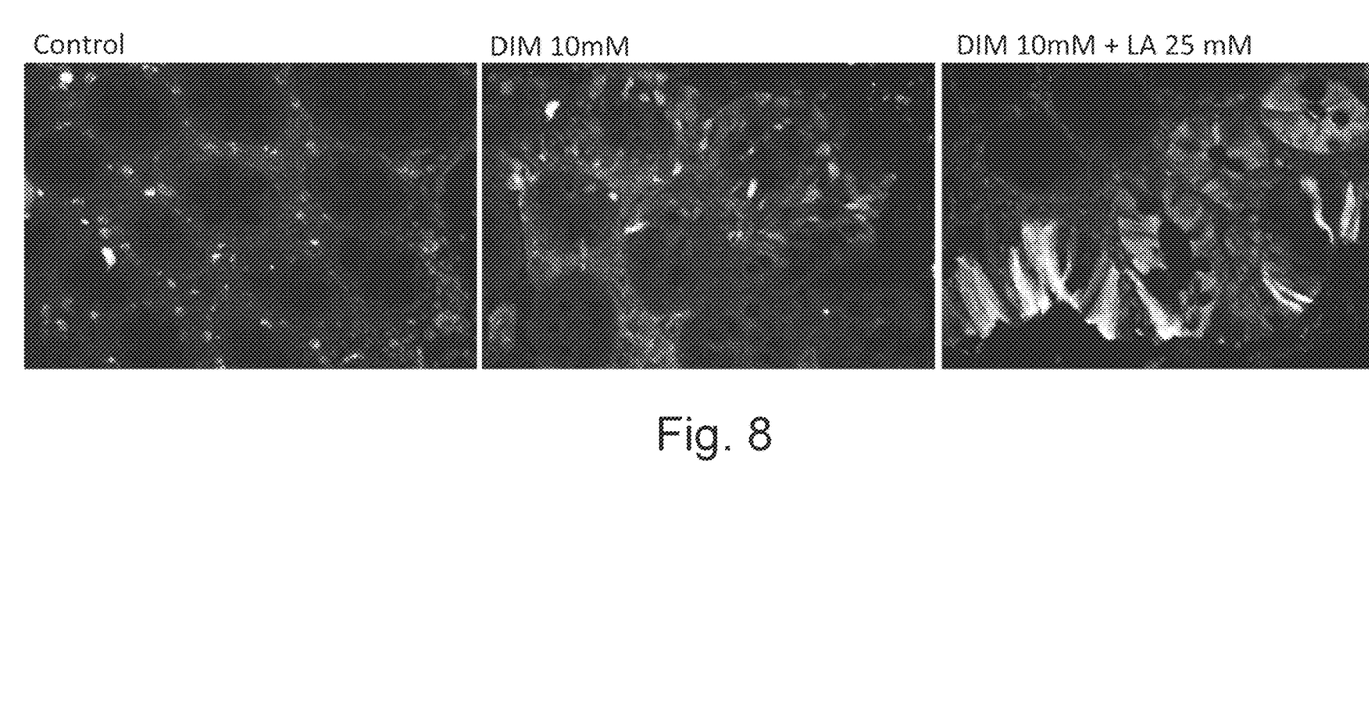
FIG. 8 shows GPR84 agonist 3,3'-diindolylmethane (DIM) potently activates pERK in combination with GPR120 agonist TUG891 and GPR84 agonist lauric acid.
Figure 9:
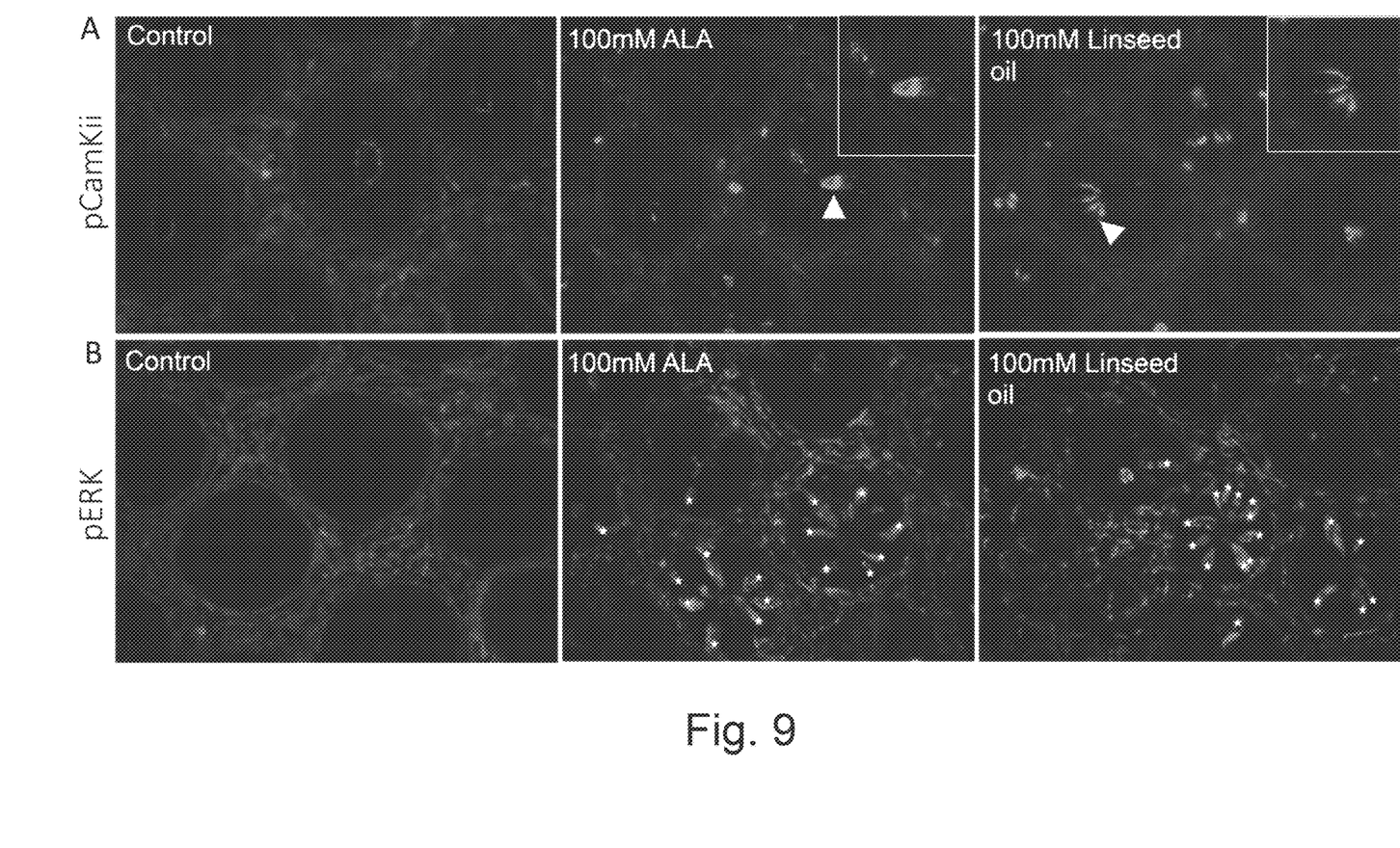
FIG. 9 shows naturally occurring GPR120 agonists α-linolenic acid (ALA) and linseed oil potently induce expression of cell activation markers pCamKii and pERK in human colonic mucosa. (a) Both ALA and linseed oil activate coloncytes via pCamKii activation, with majority of positive staining in the apical region of the cell. Arrows point to positive cell highlighted in magnified inset image. (b) A large number of colonocytes are positive for pERK as shown by the white stars when stimulated with ALA and linseed oil.

The results show GPR84 agonist 3,3'-diindolylmethane (DIM) potently activates an intracellular pathway driven by phosphorylated ERK in colonocytes, when administered in combination with GPR120 agonist TUG891 and GPR84 agonist lauric acid (FIG. 8).

EXAMPLE 6: 100 mM ALA AND LINSEED OIL ACTIVATE INTRACELLULAR PATHWAYS DRIVEN BY PHOSPHORYLATED ERK AND PHOSPHORYLATED CaMKII

Naturally occurring GPR120 agonists ALA and Linseed oil activate intracellular pathways as measured by both phosphorylated ERK and phosphorylated CaMKII in human colonic mucosa. ALA and Linseed oil have a high affinity for GPR120 but are also recognised by GPR84. ALA and Linseed oil activate both phosphorylated ERK and phosphorylated CaMKII in comparison to the selective GPR120 agonist TUG891 which only activates phosphorylated CaMKII (see Example 2) (FIG. 8).

The invention claimed is:
1. A method of treating obesity and overweight comprising administering to a subject in need thereof a composition comprising a GPR84 agonist and a GPR120 agonist, wherein the GPR84 agonist is 3,3'-diindolylmethane and wherein the GPR120 agonist is α-linolenic acid (ALA) or an ester thereof, wherein the composition is a delayed release formulation for release in the distal small intestine and large intestine.

2. The method as claimed in claim 1, in which the GPR120 agonist is from a natural source.

3. The method as claimed in claim 2, in which the natural source of GPR120 agonist is a plant seed oil.

4. The method as claimed in claim 1, wherein the composition further comprises an amino acid.

5. The method as claimed in claim 1, wherein the composition is administered orally.

6. The method as claimed in claim 1, wherein the delayed release formulation is a delayed release capsule.

7. The method as claimed in claim 6, wherein the delayed release capsule comprises a polymer of methacrylic acid and methyl methacrylate.

8. The method as claimed in claim 1, wherein the composition further comprises the GPR84 agonist lauric acid.

* * * * *